United States Patent
Bentzel

(10) Patent No.: US 7,275,441 B2
(45) Date of Patent: *Oct. 2, 2007

(54) METHOD FOR ULTRASONIC INSPECTION OF GENERATOR FIELD TEETH

(75) Inventor: Edward Lee Bentzel, Latham, NY (US)

(73) Assignee: General Electric Company, Schenectady, NY (US)

( * ) Notice: Subject to any disclaimer, the term of this patent is extended or adjusted under 35 U.S.C. 154(b) by 145 days.

This patent is subject to a terminal disclaimer.

(21) Appl. No.: 11/111,289

(22) Filed: Apr. 21, 2005

(65) Prior Publication Data

US 2006/0236767 A1  Oct. 26, 2006

(51) Int. Cl.
*G01N 29/00* (2006.01)

(52) U.S. Cl. .............. 73/643; 73/600; 73/602; 73/622

(58) Field of Classification Search .......... 73/596, 73/599, 600, 602, 643, 622, 593, 625, 628
See application file for complete search history.

(56) References Cited

U.S. PATENT DOCUMENTS

| | | | | |
|---|---|---|---|---|
| 4,457,176 A | * | 7/1984 | Scholz | 73/624 |
| 4,685,334 A | * | 8/1987 | Latimer | 73/599 |
| 5,329,230 A | | 7/1994 | Viertl et al. | 324/262 |
| 6,079,273 A | * | 6/2000 | Latimer et al. | 73/622 |
| 6,119,522 A | * | 9/2000 | Johnson et al. | 73/643 |
| 6,170,336 B1 | | 1/2001 | Johnson et al. | 73/643 |
| 6,282,964 B1 | * | 9/2001 | Hancock et al. | 73/622 |
| 6,732,587 B2 | * | 5/2004 | Lorraine et al. | 73/599 |
| 6,823,736 B1 | * | 11/2004 | Brock et al. | 73/587 |
| 6,854,332 B2 | * | 2/2005 | Alleyne | 73/636 |
| 6,896,171 B2 | * | 5/2005 | Den Boer et al. | 228/103 |
| 6,993,971 B2 | * | 2/2006 | Bossi et al. | 73/620 |
| 7,026,943 B2 | * | 4/2006 | Knowles et al. | 340/582 |
| 2004/0244490 A1 | * | 12/2004 | Turner | 73/587 |

* cited by examiner

*Primary Examiner*—Hezron Williams
*Assistant Examiner*—Jacques M. Saint-Surin
(74) *Attorney, Agent, or Firm*—Cantor Colburn LLP

(57) ABSTRACT

A method for ultrasonically inspecting a generator field tooth for the detection, characterization and/or sizing of cracks thereat is disclosed. A monolithic piezoelectric transducer (MPT) productive of a test signal having a defined angle of refraction with respect to the tooth material is selected. The MPT is positioned at an outer surface of the tooth and oriented so as to direct the test signal to propagate through the tooth toward a load surface of the tooth where a butt joint of a set of wedges is disposed. The MPT is activated so as to test the load surface proximate the butt joint for cracks thereat.

22 Claims, 12 Drawing Sheets

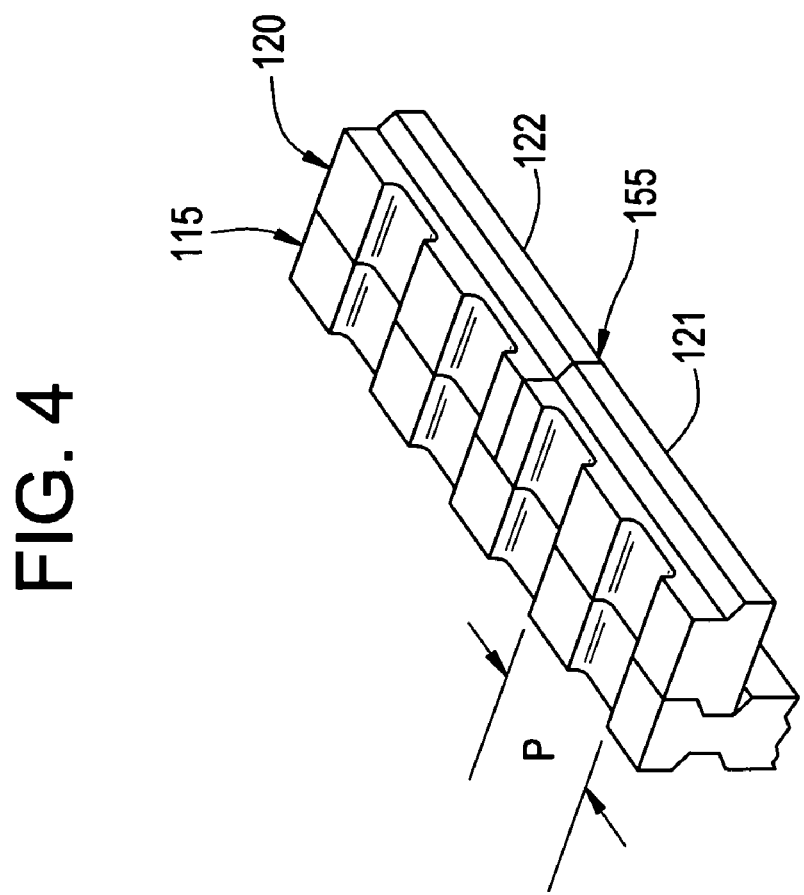
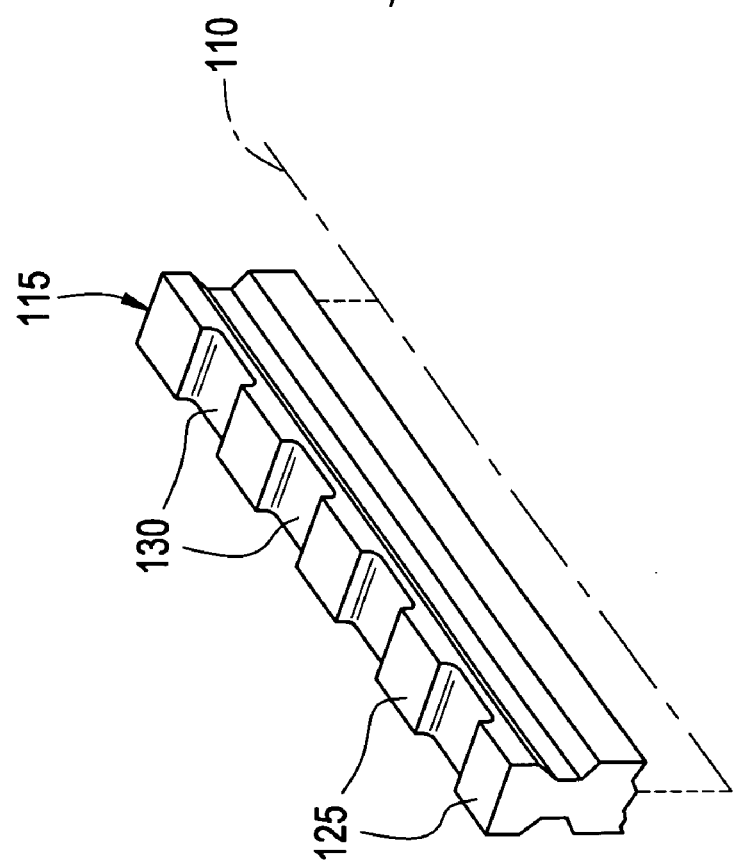

_US 7,275,441 B2_

METHOD FOR ULTRASONIC INSPECTION OF GENERATOR FIELD TEETH

BACKGROUND OF THE INVENTION

The present disclosure relates generally to a method for inspecting generator field teeth, and particularly to a method for inspecting generator field teeth for the detection, characterization and/or sizing of cracks thereat.

Typical generators used to produce electrical power employ rotor shafts having field teeth and wedges for retaining the field conductors. Typical field teeth and wedge designs employ a plurality of wedges that are arranged in a butt joint fashion along the length of an adjacent tooth, and dovetail engagement surfaces that serve to constrain the wedges during rotation of the rotor. During operation, movement of the wedges causes relative movement across the butt joint of two adjacent wedges, which in turn may cause fretting on the load surface of the tooth that is serving to constrain outward radial movement of the wedges. Fretting on the load surfaces at the butt joint between wedges can cause crack initiation at this location.

Accordingly, there is a need in the art for a method of inspecting generator field teeth for the detection, characterization and/or sizing of cracks that may occur at fretted load surfaces in an efficient and economical manner.

BRIEF DESCRIPTION OF THE INVENTION

Embodiments of the invention include a method for ultrasonically inspecting a generator field tooth for the detection, characterization and/or sizing of cracks thereat. A monolithic piezoelectric transducer (MPT) productive of a test signal having a defined angle of refraction with respect to the tooth material is selected. The MPT is positioned at an outer surface of the tooth and oriented so as to direct the test signal to propagate through the tooth toward a load surface of the tooth where a butt joint of a set of wedges is disposed. The MPT is activated so as to test the load surface proximate the butt joint for cracks thereat.

Other embodiments of the invention include a method for ultrasonically inspecting a generator field tooth for the detection, characterization and/or sizing of cracks thereat. A monolithic piezoelectric transducer (MPT) productive of a test signal is positioned at an outer surface of the tooth and oriented so as to direct the test signal to propagate through the tooth from a point of entry at the tooth outer surface toward a region of interest on a horizontal centerline of a load surface of the tooth at a defined distance from the point of entry. The MPT is activated so as to test the load surface for cracks at the region of interest.

Further embodiments of the invention include a method for selecting a monolithic piezoelectric transducer (MPT) capable of producing a test signal for inspecting a generator field tooth for the detection, characterization and/or sizing of cracks at a region of interest of the tooth. A direction vector is defined for the test signal in the tooth such that the test signal is directed from a point of entry at a tooth outer surface to the region of interest. A skew angle and an angle of refraction are defined that will result in the test signal following the defined direction vector. An MPT is selected with the desired angle of refraction capable of providing the test signal at the defined direction vector.

BRIEF DESCRIPTION OF THE DRAWINGS

Referring to the exemplary drawings wherein like elements are numbered alike in the accompanying Figures:

FIGS. 3 and 4 depict isometric views of a portion of the generator field of FIG. 1 with additional detail provided;

DETAILED DESCRIPTION OF THE INVENTION

An embodiment of the invention provides an ultrasonic method for inspecting a generator field tooth for the detection, characterization and/or sizing of cracks thereat. An embodiment of the method involves: selecting a test signal generator productive of a test signal suitable for the test under study; positioning the signal generator at a defined location; orienting the signal generator so as to direct the test signal to propagate through the tooth toward a region of interest of the tooth; and activating the signal generator so as to test the region of interest for cracks thereat.

In an embodiment, the signal generator is an electromagnetic acoustic transducer (EMAT). In another embodiment, the signal generator is a monolithic piezoelectric transducer (MPT). In an embodiment, a transducer is selected that is capable of a pulse-echo mode of testing, that is, one transducer produces and transmits the ultrasonic signal and the same transducer receives the reflected signal for subsequent analysis.

Figure 1:
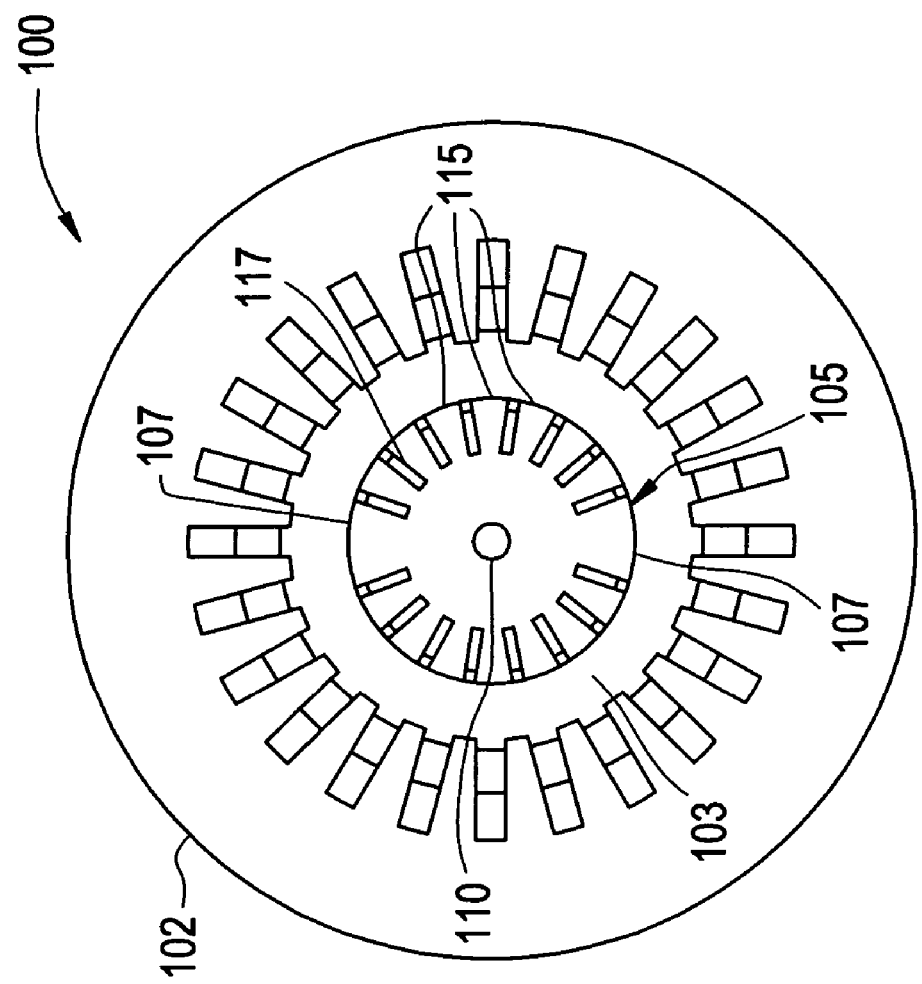
FIG. 1 depicts an end view of an exemplary generator with some detail removed for clarity.

FIG. 1 depicts a cross section end view of a typical generator 100 having a rotor, or field, 105 with an axis of rotation 110. The field 105 rotates within a stator 102 with an airgap 103 therebetween. The field 105 includes field poles 107 and a plurality of field teeth 115 that are separated by field slots 117. A plurality of sets of wedges 120, best seen by referring to FIG. 2, which depicts an expanded view of a portion of FIG. 1 that includes two teeth 115 and two wedges 120, are disposed within field slots 117. The plurality of field teeth 115 extend radially outward with respect to the axis of rotation 110 and have an elongated profile that extends parallel to the axis of rotation 110, best seen by referring to FIGS. 3 and 4, where FIG. 3 depicts a single tooth 115 and FIG. 4 depicts a single tooth 115 and wedges 121, 122.

Figure 2:
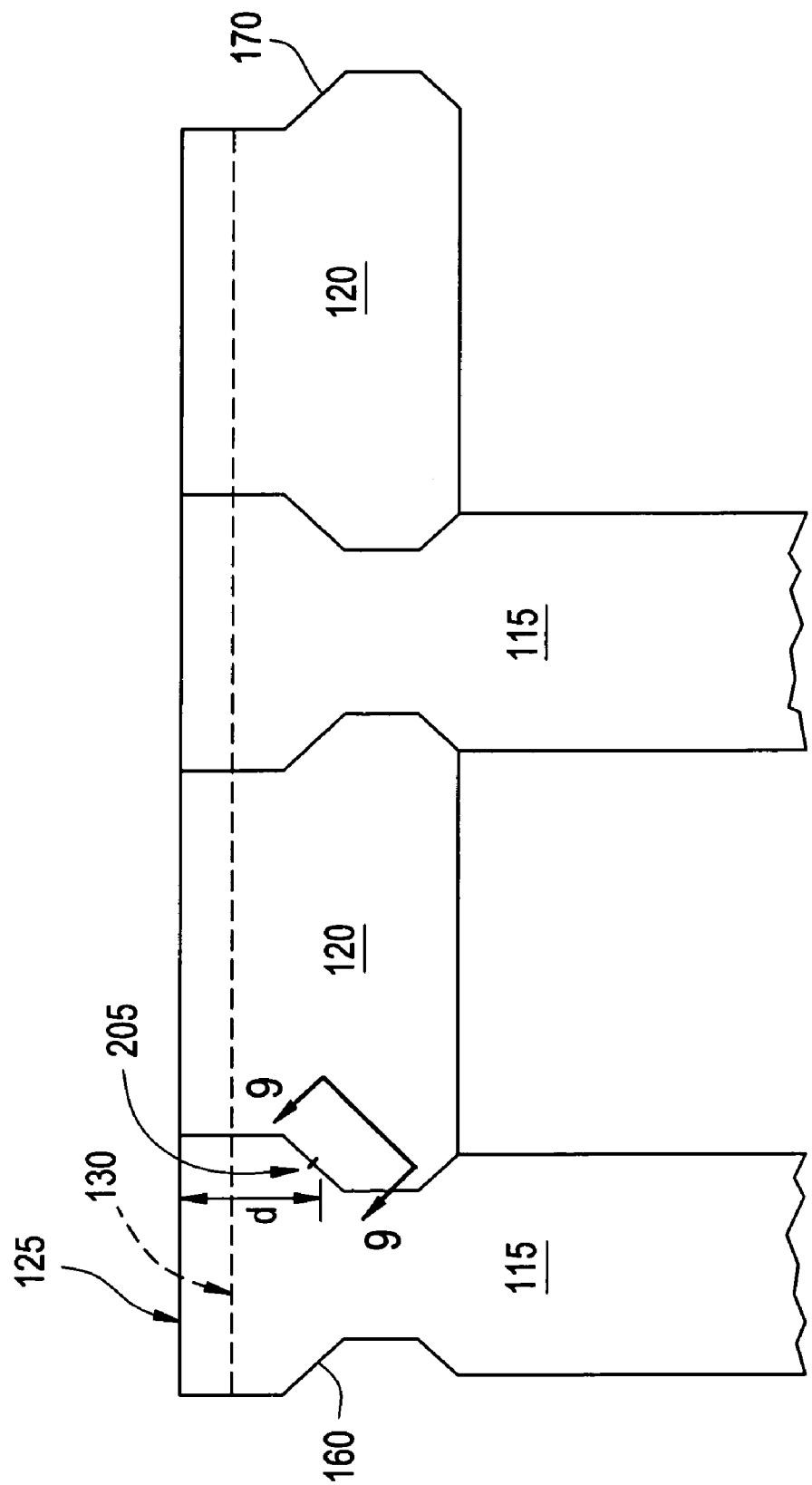
FIG. 2 depicts an end view of a portion of the generator field of FIG. 1 with additional detail provided.
Figure 5:
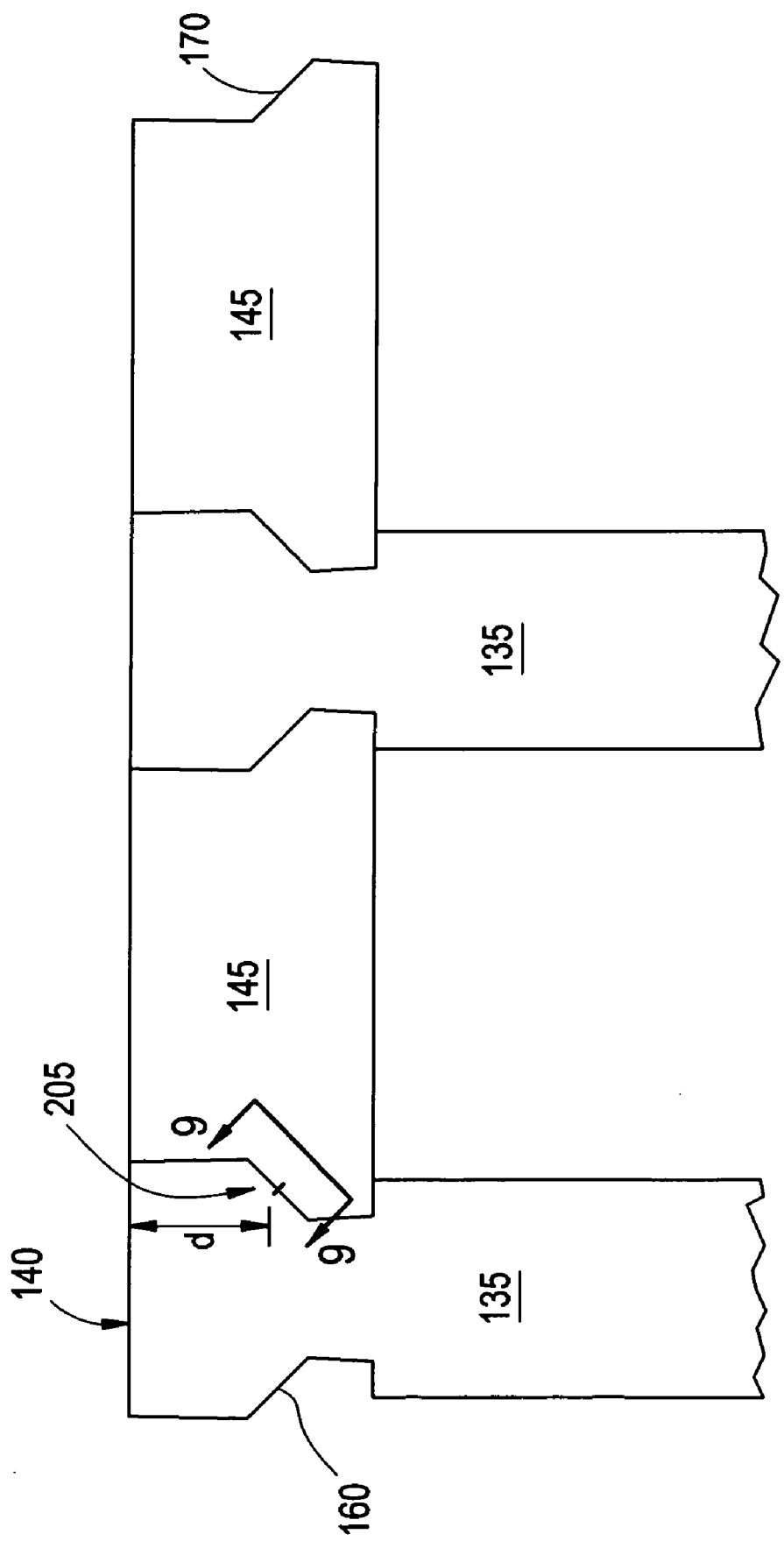
FIG. 5 depicts an alternative end view to the end view depicted in FIG. 2.
Figure 7:
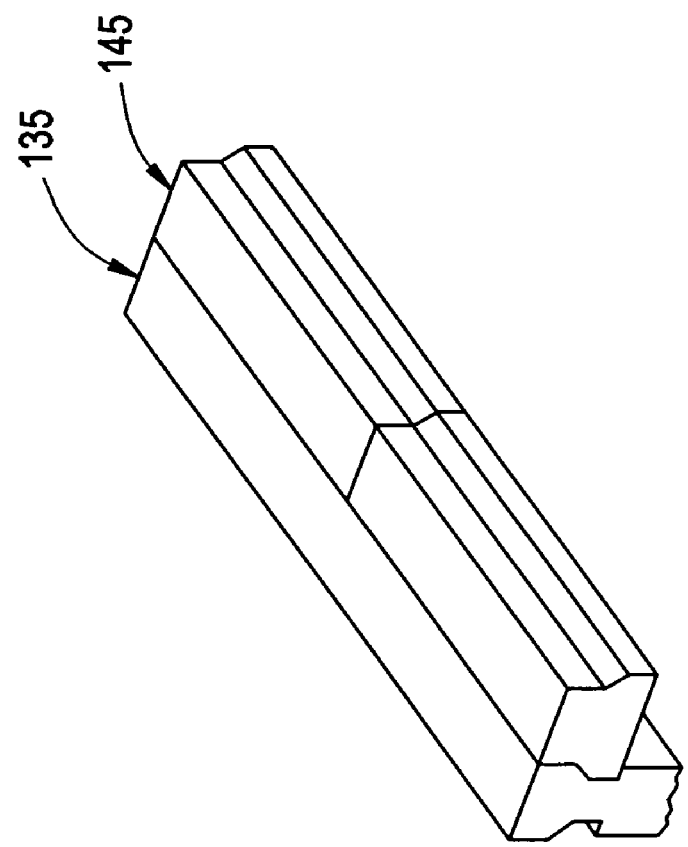
FIGS. 6 and 7 depict alternative isometric views to those depicted in FIGS. 3 and 4.
Figure 6:
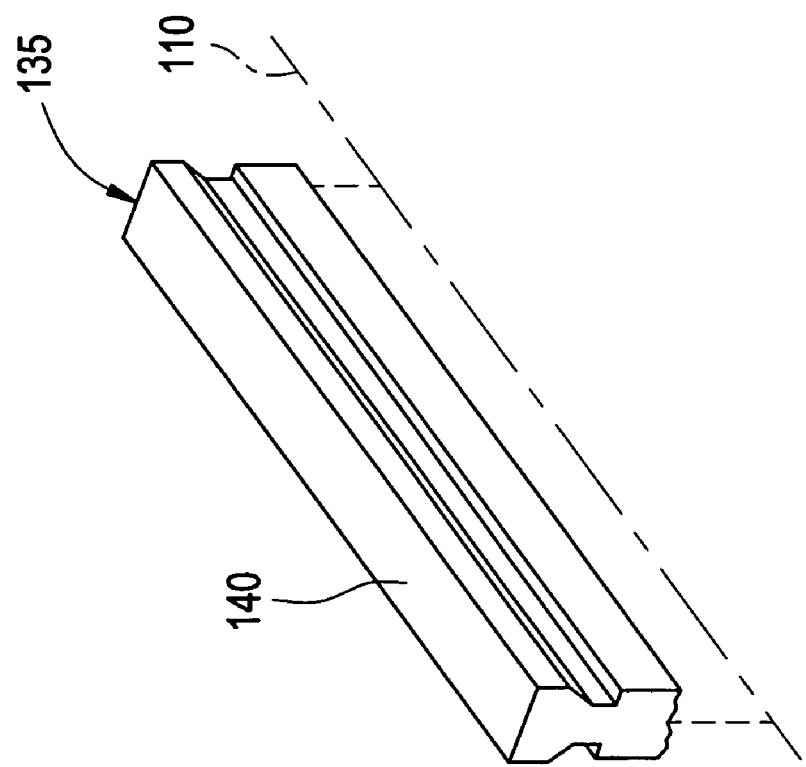

FIGS. 2-4 depict teeth 115 having land outer surfaces 125 and groove outer surfaces 130, with the wedges 120 having detail to match. For illustration purposes, it will be appreciated that only very basic wedge detail is shown for wedges 120, and that for simplification, FIGS. 2-4 do not show additional detail such as cooling slots or holes that the wedges 120 may contain. An alternative arrangement to that of FIGS. 2-4 is depicted in FIGS. 5-7 that may employ teeth 135 (illustrated in block form for clarity) having a largely continuous outer surface 140, with the wedges 145 having detail to match, illustrated in basic detail only as previously discussed.

Figure 8:
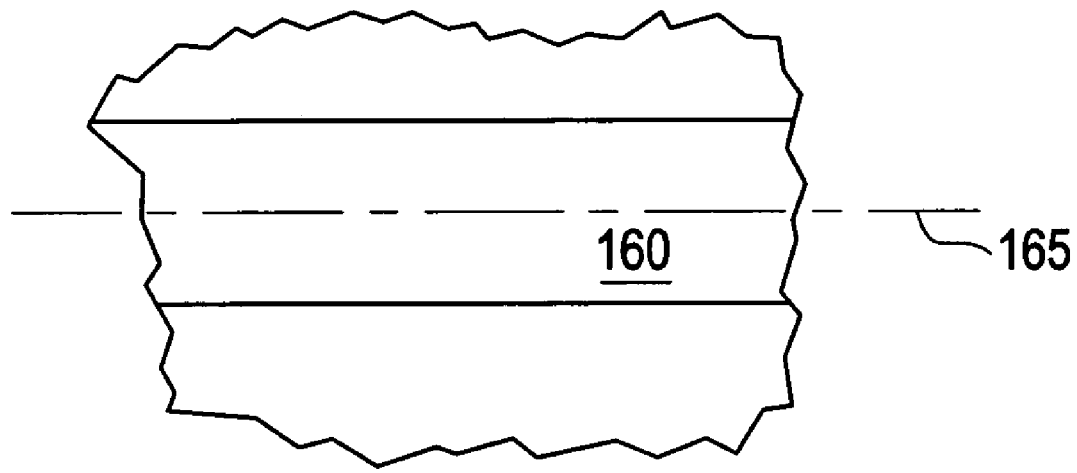
FIG. 8 depicts a face oriented view of a load surface of a field tooth similar to those depicted in FIGS. 2-8.

Referring back to FIGS. 2-4, the plurality of sets of wedges 120 are disposed between adjacent teeth 115, with each set of wedges 120 having at least two wedges 121 and 122 disposed end to end parallel to the axis of rotation 110 so as to form a butt joint 155 between adjacent ends. Teeth 115, 135, whether they have a land 125 and a groove 130 outer surface or a continuous outer surface 140, each have a load surface 160 (best seen by referring to FIGS. 2 and 5) having boundaries that define a horizontal centerline 165 (best seen by referring to FIG. 8) at a vertical distance "d" down from the land outer surface 125 or the continuous outer surface 140. Each wedge 120, 145 has a bearing surface 170 disposed proximate the load surface 160 such that in response to rotation of the rotor 105, the bearing surfaces 170 bear against the load surfaces 160 of each tooth 115, 135, whereby the wedge 120, 145 is restrained from outward radial movement and the load surface 160 experiences a load stress. As a result, fretting may occur at the load surface 160.

From the foregoing discussion, it will be appreciated that the method disclosed herein and discussed in more detail below is not limited to a particular configuration of tooth 115, 135. Also, while FIG. 4 depicts butt joint 155 being disposed proximate the center of a land outer surface 125 of tooth 115, the butt joint 155 may also be disposed proximate the center of a groove outer surface 130 of tooth 115, as will become evident later on.

In an embodiment having land 125 and groove 130 outer surfaces, the lands 125 and grooves 130 are disposed at a pitch "p" lengthwise along the tooth 115, best seen by referring to FIG. 4.

Figure 9:
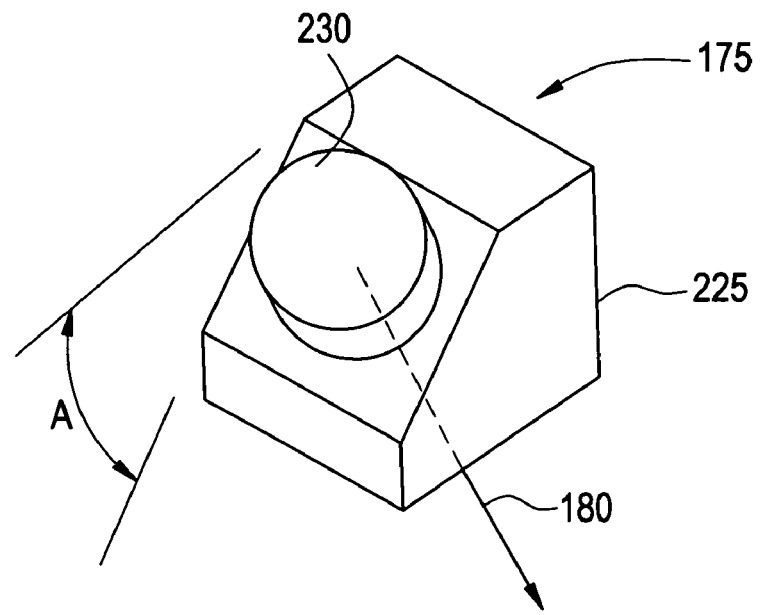
FIG. 9 depicts an isometric view of a signal generator for use in accordance with an embodiment of the invention.
Figure 10:
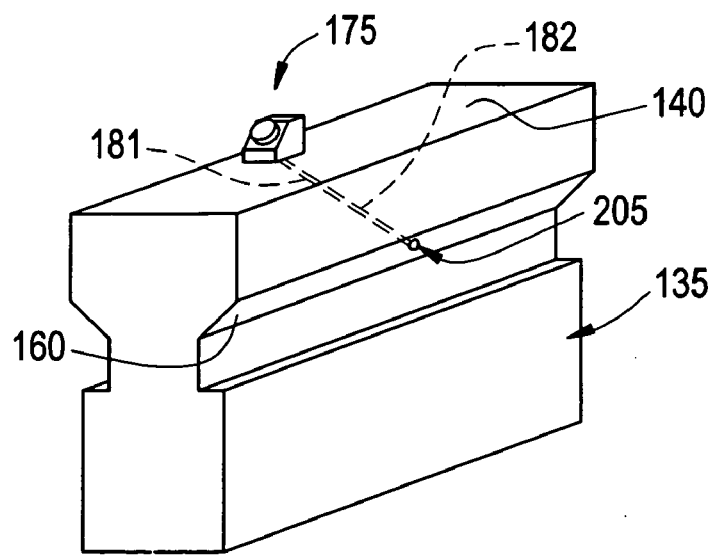
FIG. 10 depicts in isometric view the signal generator of FIG. 9 on the generator field of FIG. 5.

An exemplary method of testing for cracks at load surface 160 is accomplished by the appropriate selection of a signal generator, such as an EMAT or a monolithic piezoelectric transducer, the appropriate positioning of the signal generator, the appropriate orientation of the signal generator, and then the activation of the signal generator. FIG. 9 depicts an exemplary signal generator 175 for practicing the exemplary methods disclosed herein, where the arrow 180 represents the direction of an outgoing ultrasonic signal, and FIG. 10 depicts in isometric view signal generator 175 disposed on outer surface 140 of the tooth 135 of FIG. 5, showing outgoing and reflected signal lines 181, 182 to/from a region of interest (such as a crack for example) 205 on load surface 160. For illustration purposes, the signal generator 175 illustrated in FIG. 9 has two components, a support 225, which in an embodiment is made of Plexiglas, and a piezoelectric element 230 mounted on the support 225. The angle "A" of the support 225 ultimately establishes the angle of refraction of the signal in the material being inspected.

In FIG. 9, signal generator 175 is more representative of a MPT, which uses angle "A" of the support 225 to establish the angle of refraction of the signal. In contrast, an EMAT does not necessarily require a support 225 to produce a signal at some angle of refraction. In an EMAT, the angle of refraction of the signal may be established through other means, such as by using phasing circuitry. However, if phasing circuitry is not employed, support 225 may be used to establish the angle of refraction of the signal in the material to be inspected, where support 225 is made of a material suitable for the intended purpose, such as metal for example. From the foregoing, it will be appreciated that while FIG. 9 is more illustrative of a MPT signal generator 175, it may in principle also be illustrative of an EMAT signal generator 175. Accordingly, reference herein to signal generator 175 is intended to be a reference to either a MPT or an EMAT.

Figure 11:
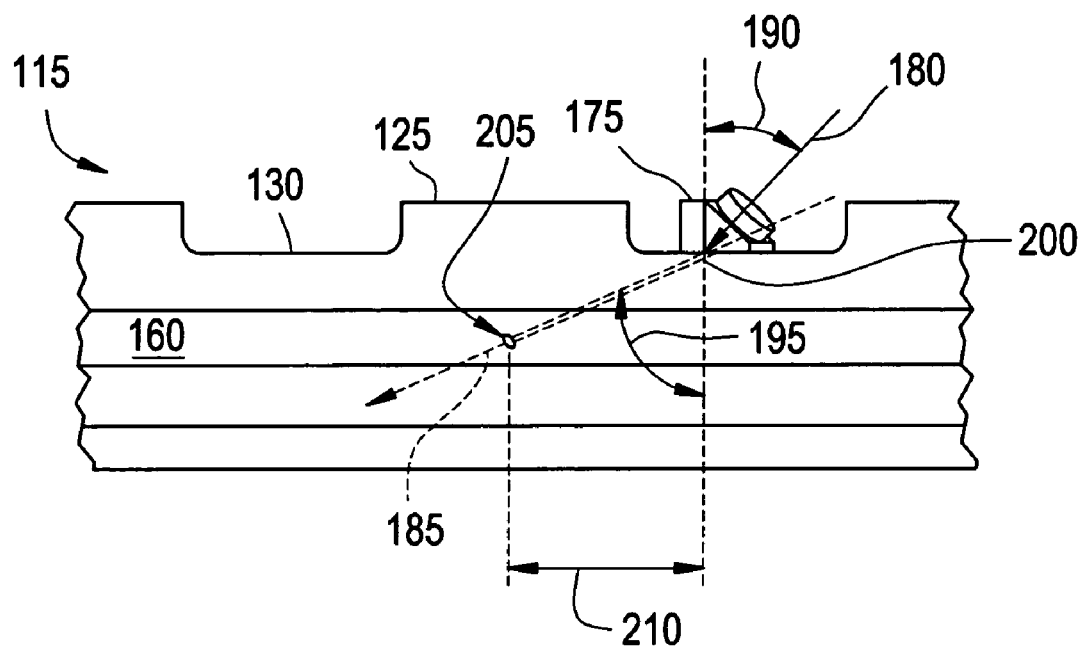
FIGS. 11-19 depict various views for practicing an embodiment of the invention.

Commercially available off the shelf (COTS) signal generators 175 have operational characteristics that include a characteristic angle of refraction that is associated with the outgoing signal 180 as it passes into the material of a field tooth 115, 135. This characteristic is illustrated in FIG. 11, which depicts a side view of a portion of a tooth 115 having a signal generator 175 disposed on a groove outer surface 130. The signal generator 175 is illustrated having an outgoing signal 180 incident on an outer surface 130 (or alternatively 125, 140) of a tooth 115 (or alternatively 135), and a refracted signal 185 propagating through the tooth 115 along a defined direction vector (also depicted generally by reference numeral 185).

With reference still to FIG. 11, the angle of incidence is represented by reference numeral 190, and the angle of refraction is represented by reference numeral 195. The entry point of the ultrasonic signal 180 into the tooth material is represented by reference numeral 200. The region of interest, such as a crack on load surface 160, is represented by reference numeral 205 (also depicted as a short vertical line). The distance along the length of tooth 115 from the point of signal entry 200 to the region of interest 205 is defined as the axial distance and is represented by reference numeral 210.

Figure 12:
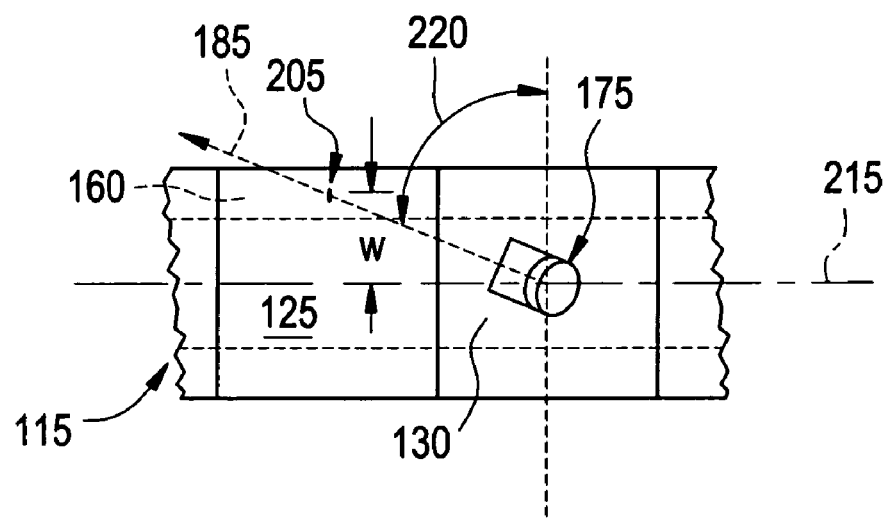

Referring now to FIG. 12, which depicts a top view of the arrangement illustrated in FIG. 11, signal generator 175 is depicted being disposed proximate, but not necessarily on, the longitudinal centerline 215 of the tooth 115. However, since the region of interest 205 is positioned off of the longitudinal centerline 215, on load surface 160, the signal generator 175 is skewed sideways, thereby defining a skew angle 220 at which refracted signal 185 propagates. Accordingly, the skew angle 220 is dependent on both the axial distance 210 and the lateral position of the signal generator 175 on the outer surface of the tooth.

In the event of a stepped tooth 115, having land 125 and groove 130 outer surfaces, butt joint 155 may be located proximate a land outer surface 125 or a groove outer surface 130, and more specifically, butt joint 155 may be located proximate the middle of a land outer surface 125 or the middle of a groove outer surface 130. In testing for cracks in any of these situations, the signal generator 175 may be positioned at either a land outer surface 125 or a groove outer surface 130, which is illustrated in FIGS. 13-16.

Figure 13:
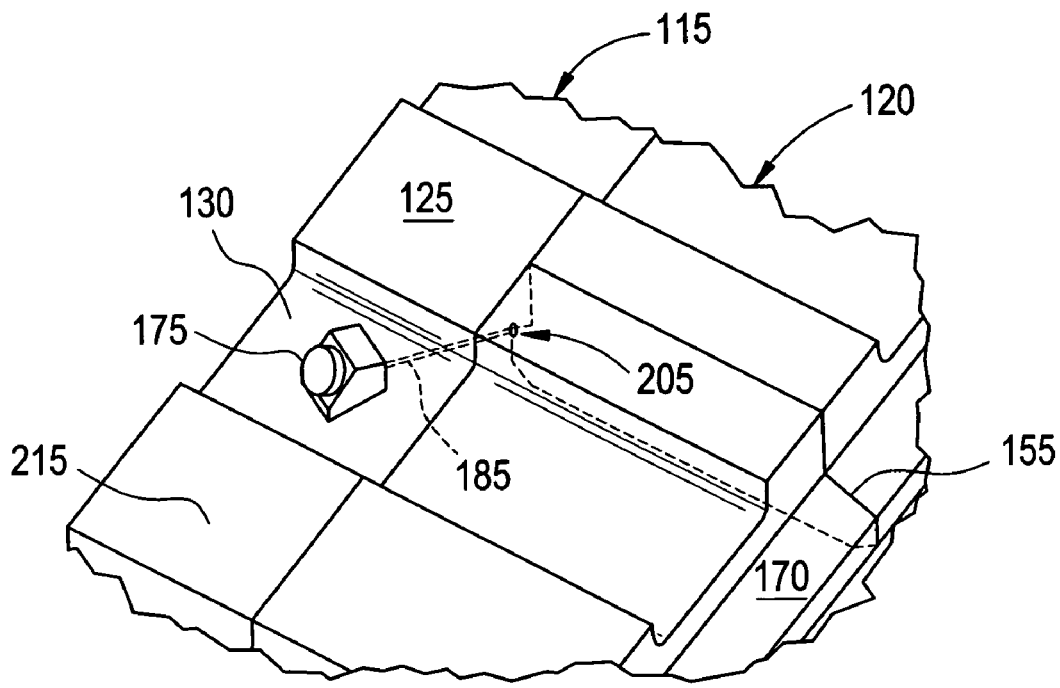

In FIG. 13, butt joint 155 is disposed proximate the middle of land outer surface 125, and signal generator 175 is disposed proximate, but not necessarily on, the longitudinal centerline 215 of tooth 115 on groove outer surface 130. The refracted signal 185 propagates along a direction vector inside the material of tooth 115 to the region of interest 205, which is on the horizontal centerline 165 (see FIG. 8) of load surface 160 proximate the butt joint 155.

In FIG. 14, butt joint 155 is again disposed proximate the middle of land outer surface 125, but here signal generator 175 is disposed offset from the longitudinal centerline 215 of tooth 115 on land outer surface 125. The refracted signal 185 propagates along a direction vector inside the material of tooth 115 to the region of interest 205, which is on the horizontal centerline 165 (see FIG. 8) of load surface 160 proximate the butt joint 155.

Figure 15:
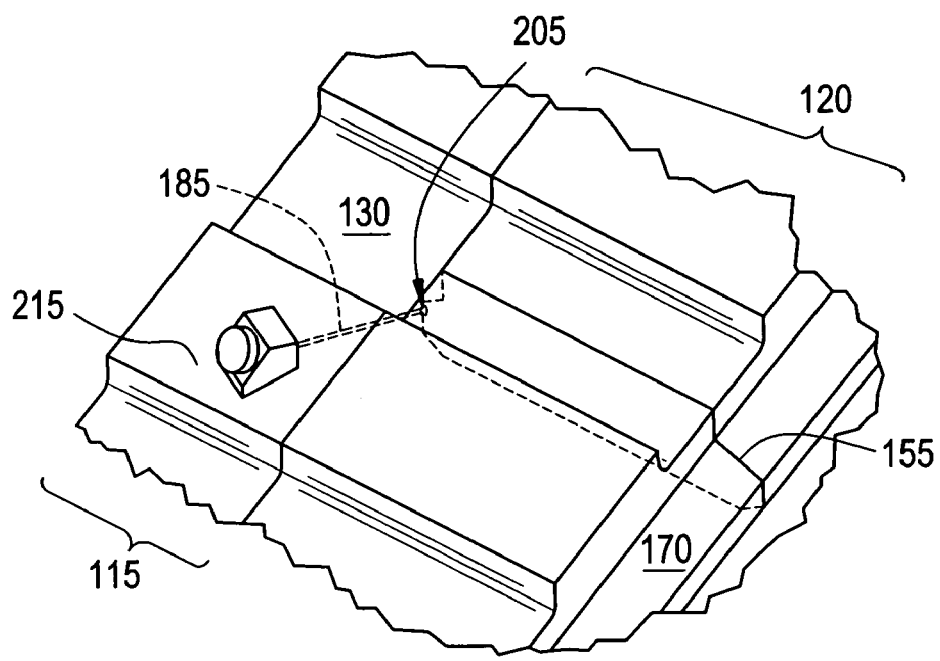

In FIG. 15, butt joint 155 is disposed proximate the middle of groove outer surface 130, and signal generator 175 is disposed offset from the longitudinal centerline 215 of tooth 115 on land outer surface 125. The refracted signal 185 propagates along a direction vector inside the material of tooth 115 to the region of interest 205, which is on the horizontal centerline 165 (see FIG. 8) of load surface 160 proximate the butt joint 155.

In FIG. 16, butt joint 155 is again disposed proximate the middle of groove outer surface 130, but here signal generator 175 is disposed proximate, but not necessarily on, the longitudinal centerline 215 of tooth 115 on groove outer surface 130. The refracted signal 185 propagates along a direction vector inside the material of tooth 115 to the region of interest 205, which is on the horizontal centerline 165 (see FIG. 8) of load surface 160 proximate the butt joint 155.

In view of the foregoing description, exemplary methods for testing for cracks at load surface 160 will now be discussed.

A signal generator 175 productive of a test signal 180 having a defined angle of refraction 195 with respect to the tooth material is selected. The signal transducer 175 is positioned at an outer surface of the tooth 115, which in accordance with the previous discussion may be a land outer surface 125, a groove outer surface 130, or a continuous outer surface 140. In the event that signal generator 175 is an EMAT, the signal generator 175 is positioned on the tooth 115 absent a fluid couplant. In the event that signal generator 175 is a monolithic piezoelectric transducer, the signal generator may be positioned on the tooth 115 using either a free-flowing or a non free-flowing couplant. As used herein, the term free-flowing couplant refers to an ultrasonic couplant that has fluid properties that permit the couplant to freely flow under normal test conditions of a type typically employed for testing generator field teeth, such as normal test temperature, humidity and pressure, for example. The signal generator 175 is oriented so as to direct the test signal 185, which is the refracted signal 185 inside the tooth material, to propagate through the tooth toward the load surface 160 where the butt joint 155 is disposed. Once oriented, the signal generator 175 is activated so as to test the load surface 160 proximate the butt joint 155 for cracks thereat. To assure a thorough inspection of the load surface, the signal generator 175 is then moved laterally across the tooth outer surface 125, 130, 140 on which it is positioned while keeping the skew angle fixed.

In an embodiment, orienting the signal generator 175 means orienting the signal generator 175 so as to cause the test signal 185 to propagate through the tooth 115 toward the horizontal centerline 165 of the load surface 160 where the butt joint 155 is disposed.

In the event that the outer surface of the tooth is a continuous outer surface 140 (here, the tooth is tooth 135), the axial distance 210 from the point of signal entry 200 to the region of interest 205 is primarily a function of the angle of refraction of the selected signal generator 175. Once in position on the tooth 115, the test signal 185 propagates through the axial distance 210. By defining the skew angle 220 and the angle of refraction 195, the test signal 185 will then have a defined direction vector through which it propagates in the material of the tooth 135.

In the event that the outer surface of the tooth is a stepped surface having land 125 and groove 130 outer surfaces at the defined pitch p in a direction parallel to the axis of rotation 110 (here, the tooth is tooth 115), the axial distance 210 will then be defined as a function of the pitch p. As before, once in position on the tooth 115, the test signal 185 propagates through the axial distance 210. Also as before, by defining the skew angle 220 and the angle of refraction 195, the test signal 185 will then have a defined direction vector through which it propagates in the material of the tooth 115.

With a stepped tooth 115, and in the event that the butt joint 155 is disposed proximate a land surface 125, the signal generator 175 may be positioned at a groove outer surface 130 at a distance of about p/2 from the butt joint 155, or the signal generator 175 may be positioned at a land outer surface 125 proximate the butt joint 155. In the event that the butt joint 155 is disposed proximate a groove outer surface 130 (again where the tooth is stepped), the signal generator 175 may be positioned at a land outer surface 125 at a distance of about p/2 from the butt joint 155, or the signal generator 175 may be positioned at a groove outer surface 130 proximate the butt joint 155.

Figure 14:
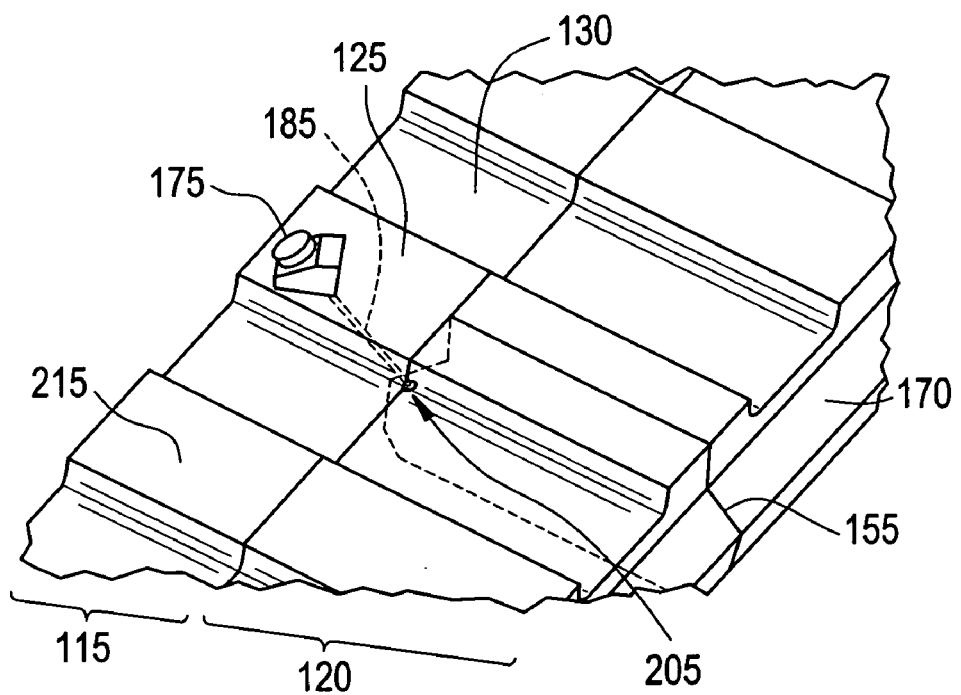
Figure 16:
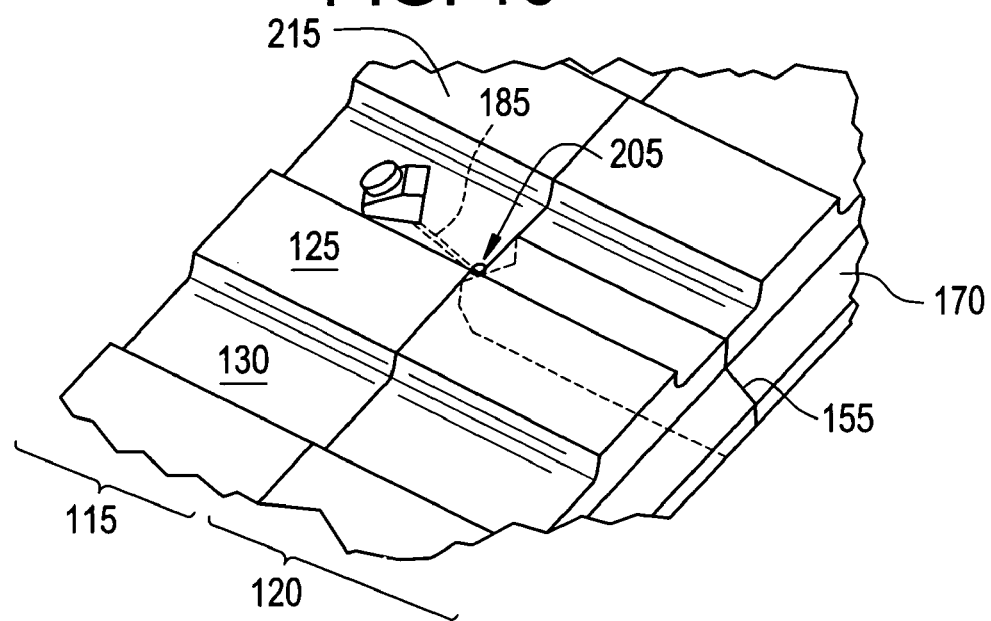

It will be appreciated from the foregoing discussion and the various illustrations provided herein that a first test orientation for the signal generator 175 is defined in response to the signal generator 175 being disposed at a distance of about p/2 from the butt joint 155 (see FIGS. 13 and 15 for example), and a second test orientation for the signal generator 175 is defined in response to the signal generator 175 being disposed at a distance of less than p/2 from the butt joint 155 (see FIGS. 14 and 16 for example). As will be appreciated, the second test orientation is at an orientation other than the first test orientation.

At the first test orientation, the signal generator 175 when placed on the groove outer surface 130 is disposed proximate, but not necessarily on, the longitudinal centerline 215 of the tooth 115, and when placed on the land outer surface 125 is disposed offset from the longitudinal centerline 215 of the tooth 115.

At the second test orientation, the signal generator 175 when placed on the groove outer surface 130 is disposed proximate, but not necessarily on, the longitudinal centerline 215 of the tooth 115, and when placed on the land outer surface 125 is disposed offset from the longitudinal centerline 215 of the tooth 115.

By employing an embodiment of signal generator 175 having well defined test orientations, and being capable of testing for cracks at a load surface 160 of a field tooth 115, 135 absent a fluid couplant, or at least absent a free-flowing couplant, the exemplary methods of testing described herein may be suitable for robotic implementation.

It will be appreciated that the aforementioned descriptions and illustrations relating to ultrasonic inspection of a "stepped" field tooth 115 have been made with reference to the outlet cooling sections of a generator 100, which are the sections that have a regular alternating pattern of lands 125 and grooves 130. However, embodiments of the invention are not so limited, and may also apply to ultrasonic inspection of the inlet cooling sections of the generator 100, which contain groove locations as previously discussed, but the land locations also contain narrow "inlet" grooves that are centered on the lands, which is best seen by now referring to FIGS. 17 and 18.

Figure 17:
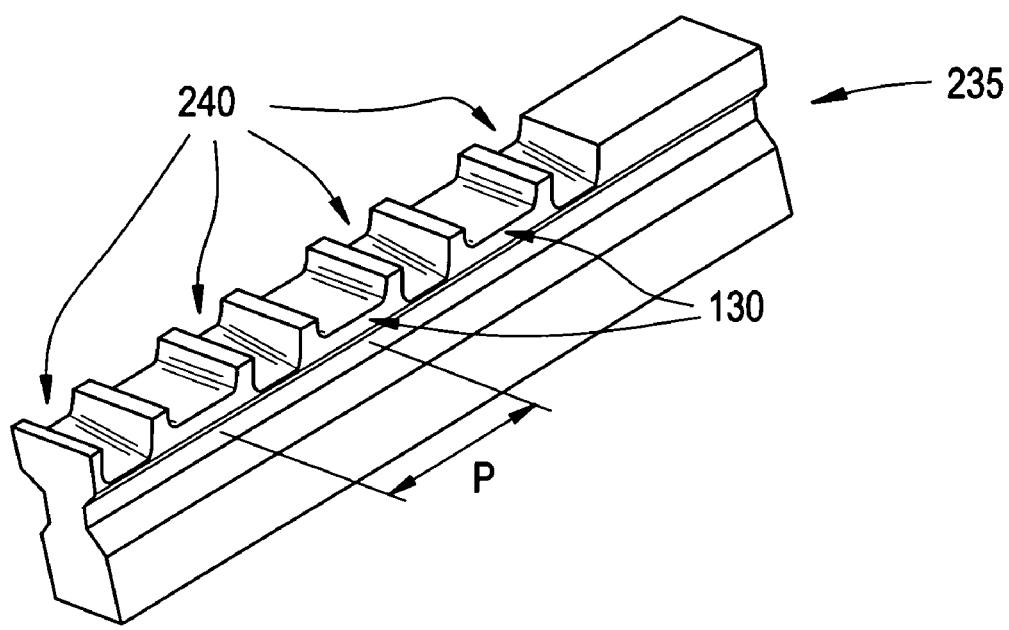
Figure 18:
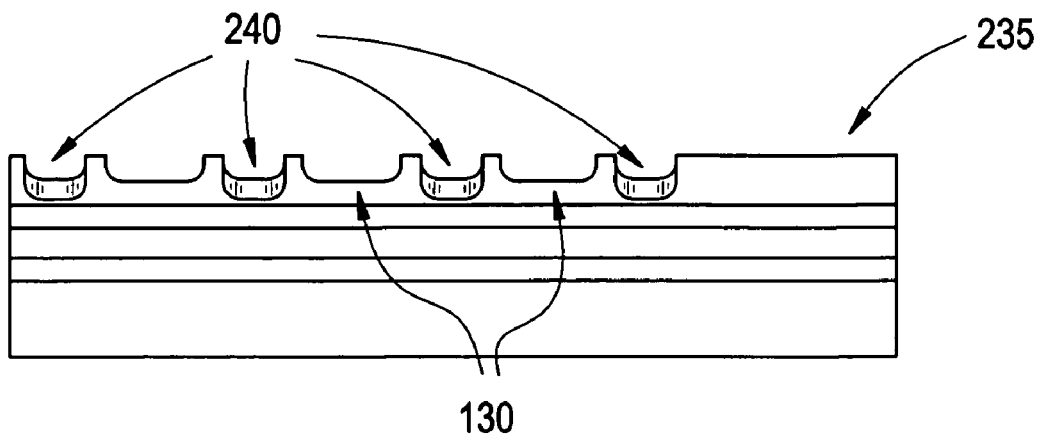

In FIGS. 17 and 18, a stepped field tooth 235 suitable for the inlet cooling section of generator 100 is depicted having groove outer surfaces 130 (as previously described) and inlet grooves 240 that have been cut into the original land outer surfaces. As can be seen, inlet grooves 240 are cut or machined at an angle (slant) from one side of the tooth to the other, which is unlike grooves 130 that are cut straight across the tooth. In an embodiment, the angle of slant of inlet grooves 240 is constant throughout the generator field 105. The pitch "p" of grooves 130 is as described above for the outlet section.

Figure 19:
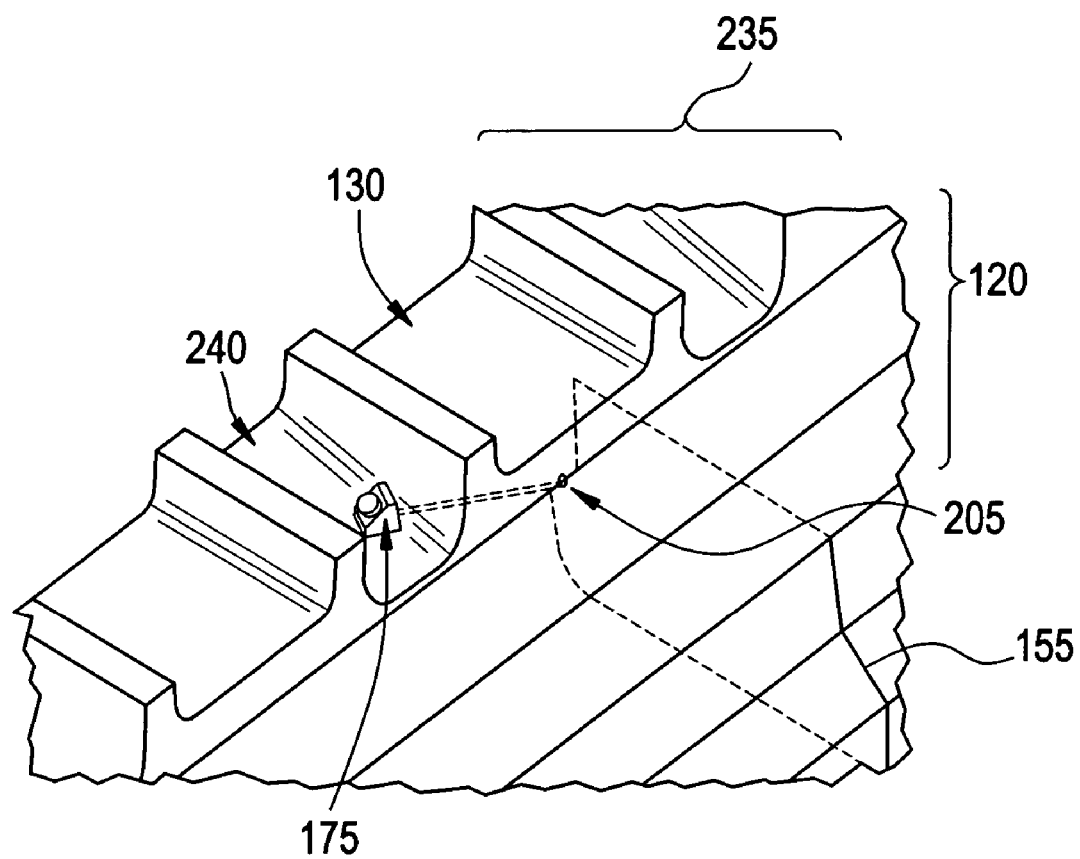

The same general inspection method as previously described with reference to the outlet cooling sections also applies to the inlet cooling sections. In the inlet cooling sections, however, the butt joints 155 occur at the center of one of the larger regular groove locations 130, which is best seen by now referring to FIG. 19. In FIG. 19, it is seen that the signal generator 175 is positioned in an inlet groove 240 that is adjacent the butt joint 155 to be inspected. It will be appreciated that since the inlet groove 240 is slanted from one side of the tooth to the other, different direction vectors are involved for the test signal when inspecting the same butt joint location on opposite sides of the tooth, since the vertical distance "d" from the tooth land surface down to the center of the load surface 160 is different from the "high" side of the inlet groove than from the "low" side of the inlet groove. Accordingly, the direction vectors to inspect from the inlet grooves 240, and therefore the angle of refraction and the skew angle, are dependent on the slant of the inlet groove surface and the side of the tooth being inspected.

As disclosed, some embodiments of the invention may include some of the following advantages: use of an ultrasonic signal generator for the inspection and characterization of cracks at the load surface of field teeth in the vicinity of a wedge butt joint absent the need for a fluid couplant, or at least absent the need for a free-flowing couplant; a test methodology for the purpose disclosed herein that is defined by the dimensional characteristics of the field teeth, thereby enabling the use of lookup table test procedures for selecting the signal generator to be used and for defining the test orientation to be employed; and, a test methodology designed with a specific interest in being able to effectively analyze fretted load surfaces at wedge butt joint locations.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A method for ultrasonically inspecting a generator field tooth for the detection, characterization and/or sizing of cracks thereat, the generator having a rotor with an axis of rotation, the rotor having a plurality of field teeth extending radially outward with respect to the axis of rotation and having an elongated profile that extends parallel to the axis of rotation, the rotor having a plurality of sets of wedges disposed between adjacent teeth, a set of wedges having at least two wedges disposed end to end parallel to the axis of rotation so as to form a butt joint between adjacent ends, the teeth having an outer surface, and a load surface having boundaries that define a horizontal centerline at a vertical distance down from the outer surface, each wedge having a bearing surface disposed proximate the load surface such that in response to rotation of the rotor, the bearing surfaces bear against the load surface of the tooth, whereby the wedge is restrained from outward radial movement and the load surface experiences a load stress whereat fretting of the load surface may occur, the method comprising:
   selecting an monolithic piezoelectric transducer (MPT) productive of a test signal having a defined angle of refraction with respect to the tooth material;
   positioning the MPT at the outer surface of the tooth;
   orienting the MPT so as to direct the test signal to propagate through the tooth toward the load surface where the butt joint is disposed; and
   activating the MPT so as to test the load surface proximate the butt joint for cracks thereat.

2. The method of claim 1, wherein:
   the orienting the MPT comprises orienting the MPT so as to cause the test signal to propagate through the tooth toward the horizontal centerline of the load surface where the butt joint is disposed.

3. The method of claim 1, further comprising:
   in response to the outer surface of a tooth being a continuous outer surface, defining an axial distance that is a function of the defined angle of refraction of the MPT; and
   positioning the MPT at the outer surface of the tooth such that the test signal propagates through the axial distance.

4. The method of claim 3, further comprising:
   defining a skew angle and an angle of reaction for the test signal such that the test signal in the tooth has a defined direction vector; and
   positioning the MPT at the outer surface such that the test signal follows the defined direction vector.

5. The method of claim 1, further comprising:
   in response to the outer surface of a tooth being a stepped surface with land and groove outer surfaces at a defined pitch p in a direction parallel to the axis of rotation, defining an axial distance that is a function of the pitch p; and
   positioning the MPT at a land or a groove outer surface such that the test signal propagates through the axial distance.

6. The method of claim 5, further comprising:
   defining a skew angle and an angle of refraction for the test signal such that the test signal in the tooth has a defined direction vector; and
   positioning the MPT at one of the land and the groove outer surface such that the test signal follows the defined direction vector.

7. The method of claim 6, further comprising:
   in response to the butt joint being disposed proximate a land outer surface, allowing the MPT to be positioned at a groove outer surface at a distance of about p/2 from the butt joint, and allowing the MPT to be positioned at a land outer surface proximate the butt joint; and
   in response to the butt joint being disposed proximate a groove outer surface, allowing the MPT to be positioned at a land outer surface at a distance of about p/2 from the butt joint, and allowing the MPT to be positioned at a groove outer surface proximate the butt joint.

8. The method of claim 1, wherein the outer surge of the teeth include land and groove outer surfaces having a defined pitch "p" in a direction parallel to the axis of rotation, the land outer surface being at a defined elevation with respect to the groove outer surface, the method further comprising:
   in response to the butt joint being disposed proximate the middle of a land outer surface, positioning the MPT at a groove outer surface proximate the longitudinal centerline of the tooth at a horizontal distance of about p/2 from the butt joint, wherein the orienting the MPT comprises orienting the MPT such that the test signal has a defined angle of refraction and defined skew angle; and establishing a test orientation of the MPT with respect to the defined angle of refraction and the defined skew angle;

wherein the activating the MPT comprises activating the MPT disposed at the groove outer surface.

9. The method of claim 8, further comprising:

in response to the butt joint being disposed proximate the middle of a groove outer surface, positioning the MPT at a land outer surface offset from the longitudinal centerline of the tooth at a horizontal distance of about p/2 from the butt joint;

wherein the orienting the MPT comprises orienting the MPT at the test orientation; and wherein the activating the MPT comprises activating the MPT disposed at the land outer surface.

10. The method of claim 8, further comprising:

in response to the butt joint being disposed proximate the middle of a land outer surface, positioning the MPT at the same land outer surface offset from the longitudinal centerline of the tooth;

wherein the orienting the MPT comprises orienting the MPT at an orientation other than the test orientation; and wherein the activating the MPT comprises activating the MPT disposed at the land outer surface.

11. The method of claim 1, wherein the outer surface of the teeth include land and groove outer surfaces having a defined pitch "p" in a direction parallel to the axis of rotation, the land outer surface being at a defined elevation with respect to the groove outer surface, the method further comprising:

in response to the butt joint being disposed proximate the middle of a groove outer surface, positioning the MPT at a land outer surface offset from the longitudinal centerline of the tooth at a horizontal distance of about p/2 from the butt joint, wherein the orienting the MPT comprises orienting the MPT such that the test signal has a defined angle of refraction and defined skew angle; and establishing a test orientation of the MPT with respect to the defined angle of refraction and the defined skew angle;

wherein the activating the MPT comprises activating the MPT disposed at the land outer surface.

12. The method of claim 11, further comprising:

in response to the butt joint being disposed proximate the middle of a land outer surface, positioning the MPT at a groove outer surface proximate the longitudinal centerline of the tooth at a horizontal distance of about p/2 from the butt joint, wherein the orienting the MPT comprises orienting the MPT at the test orientation;

wherein the activating the MPT comprises activating the MPT disposed at the groove outer surface.

13. The method of claim 11, further comprising:

in response to the butt joint being disposed proximate the middle of a groove outer surface, positioning the MPT at the same groove outer surface proximate the longitudinal centerline of the tooth;

wherein the orienting the MPT comprises orienting the MPT at an orientation other than the test orientation; and wherein the activating the MPT comprises activating the MPT disposed at the groove outer surface.

14. The method of claim 1, further comprising:

selecting an MPT capable of a pulse-echo mode of testing.

15. The method of claim 1, further comprising:

in response to the outer surface of a tooth being a stepped surface with land and groove outer surfaces at a defined pitch p in a direction parallel to the axis of rotation, and in response to the land outer surface having a slanted inlet groove to form an inlet groove surface therein, defining an axial distance that is a function of the pitch p;

defining a skew angle and an angle of refraction for the test signal such that the test signal in the tooth has a first direction vector in response to the test signal being directed to one side of the tooth, and a second different direction vector in response to the test signal being directed to the opposite side of the tooth; and positioning the MPT at an inlet groove surface such that the test signal propagates through the axial distance at one of the first and the second direction vectors.

16. The method of claim 1, where the positioning the MPT further comprises:

positioning the MPT at the outer surface of the tooth absent a free-flowing fluid couplant.

17. A method for ultrasonically inspecting a generator field tooth for the detection, characterization and/or sizing of cracks thereat, the toot having a length, the tooth having a radial height with an outer surface, the tooth having a load surface that runs lengthwise with boundaries that define a horizontal centerline at a defined distance down from the outer surface, the method comprising:

positioning a monolithic piezoelectric transducer (MPT) productive of a test signal at the outer surface of the tooth;

orienting the MPT so as to direct the test signal to propagate through the tooth from a point of entry at the tooth outer surface toward a region of interest on the horizontal centerline of the load surface at a defined distance from the point of entry; and activating the MPT so as to test the load surface for cracks at the region of interest.

18. The method of claim 17, wherein the test signal from the MPT has a characteristic angle of refraction with respect to the material of the tooth, the method further comprising:

defining a skew angle and an angle of refraction for the test signal such that the test signal in the tooth has a defined direction vector; and selecting an MPT with a characteristic angle of refraction capable of providing the test signal at the defined direction vector.

19. The method of claim 18, wherein:

the outer surface includes land and groove outer surfaces at a defined pitch p in a lengthwise direction; and the defined direction vector is a function of the pitch p and the distance down from the outer surface to the horizontal centerline.

20. A method for selecting a monolithic piezoelectric transducer (MPT) capable of producing a test signal for inspecting a generator field tooth for the detection, characterization and/or sizing of cracks at a region of interest of the tooth, the tooth having a length, the tooth having a radial height with an outer surface, the tooth having a load surface that runs lengthwise and has boundaries that define a horizontal centerline at vertical a distance down from the outer surface, the method comprising:
- defining a direction vector for the test signal in the tooth such that the test signal is directed from a point of entry at the tooth outer surface to the region of interest;
- defining a skew angle and an angle of refraction that results in the test signal that follows the defined direction vector; and
- selecting an MPT with the desired angle of refraction capable of providing the test signal at the defined direction vector.

21. The method of claim 20, wherein:
- the outer surface includes land and groove outer surfaces at a defined pitch p in a lengthwise direction; and
- the direction vector is a function of the pitch p and the distance down from the outer surface to the horizontal centerline.

22. The method of claim 20, wherein:
- the angle of refraction of the MPT is a function of the direction vector.

* * * * *